United States Patent
Aliyev et al.

(10) Patent No.: US 9,050,587 B2
(45) Date of Patent: Jun. 9, 2015

(54) CATALYST COMPOSITION AND PROCESS FOR PREPARING LINEAR ALPHA-OLEFINS

(75) Inventors: Vugar Aliyev, Riyadh (SA); Fuad Mosa, Riyadh (SA); Mohammed Al-Hazmi, Riyadh (SA)

(73) Assignees: SAUDI BASIC INDUSTRIES CORPORATION, Riyadh (SA); LINDE AG (DE)

( * ) Notice: Subject to any disclaimer, the term of this patent is extended or adjusted under 35 U.S.C. 154(b) by 150 days.

(21) Appl. No.: 12/734,982

(22) PCT Filed: Nov. 11, 2008

(86) PCT No.: PCT/EP2008/009495
§ 371 (c)(1),
(2), (4) Date: Oct. 12, 2010

(87) PCT Pub. No.: WO2009/071164
PCT Pub. Date: Jun. 11, 2009

(65) Prior Publication Data
US 2011/0054130 A1    Mar. 3, 2011

(30) Foreign Application Priority Data
Dec. 6, 2007 (EP) .................................. 07023618

(51) Int. Cl.
| | |
|---|---|
| *B01J 31/02* | (2006.01) |
| *C07C 2/02* | (2006.01) |
| *B01J 31/04* | (2006.01) |
| *B01J 31/14* | (2006.01) |
| *B01J 31/22* | (2006.01) |
| *B01J 31/38* | (2006.01) |
| *C07C 2/30* | (2006.01) |
| *C07C 2/32* | (2006.01) |
| *B01J 27/135* | (2006.01) |

(52) U.S. Cl.
CPC ................ *B01J 31/04* (2013.01); *B01J 27/135* (2013.01); *B01J 31/0212* (2013.01); *B01J 31/0252* (2013.01); *B01J 31/143* (2013.01); *B01J 31/2208* (2013.01); *B01J 31/38* (2013.01); *B01J 2231/20* (2013.01); *B01J 2531/31* (2013.01); *B01J 2531/48* (2013.01); *C07C 2/30* (2013.01); *C07C 2/32* (2013.01); *C07C 2531/14* (2013.01); *C07C 2531/22* (2013.01)

(58) Field of Classification Search
CPC .................................. B01J 31/02; C07C 2/02
USPC .......................................... 585/502; 502/117
See application file for complete search history.

(56) References Cited

U.S. PATENT DOCUMENTS

| | | | |
|---|---|---|---|
| 3,107,764 A | 10/1963 | Jezl et al. | |
| 3,330,885 A | 7/1967 | Dalton et al. | |
| 3,644,563 A | 2/1972 | Bauer et al. | |
| 3,872,072 A | 3/1975 | Halasa | |
| 4,224,182 A * | 9/1980 | Langer et al. | 502/121 |
| 4,783,573 A | 11/1988 | Shiraki et al. | |
| 5,496,783 A | 3/1996 | Chauvin et al. | |
| 6,103,654 A | 8/2000 | Commereuc et al. | |
| 7,169,961 B2 * | 1/2007 | Kobayashi et al. | 585/502 |
| 2006/0068984 A1 * | 3/2006 | Sugano et al. | 502/115 |
| 2007/0161503 A1 | 7/2007 | Briggs et al. | |

FOREIGN PATENT DOCUMENTS

| | | |
|---|---|---|
| DE | 1570668 A1 | 12/1969 |
| DE | 4338414 C1 | 11/1993 |
| EP | 1759766 A | 3/2007 |
| EP | 1783145 A | 5/2007 |
| GB | 940125 A | 10/1963 |
| GB | 1236759 A | 6/1971 |
| WO | WO 8000224 A1 | 2/1980 |
| WO | WO 03050126 A1 | 6/2003 |
| WO | WO 2007078679 A | 7/2007 |
| WO | WO 2007090412 A1 | 8/2007 |

OTHER PUBLICATIONS

International Preliminary Report on Patentability and Written Opinion for PCT/EP2008/009495, mailed Jun. 8, 2010, 11 pages.
International Search Report for PCT/EP2008/009495 mailed Mar. 17, 2009, 4 pages.
Written Opinion of the International Searching Authority for PCT/EP/2008/009495 mailed Mar. 17, 2009, 10 pages.

* cited by examiner

*Primary Examiner* — Yong Chu
*Assistant Examiner* — Sonya Wright
(74) *Attorney, Agent, or Firm* — Cantor Colburn LLP

(57) ABSTRACT

The present invention relates to a catalyst composition for the oligomerization of ethylene, comprising a transition metal compound of the general formula $MX_m(OR')_{4-m}$ or $MX_m(OOCR')_{4-m}$, wherein R' is an alkyl, alkenyl, aryl, aralkyl or cycloalkyl group, X is chlorine or bromine and m is from 0 to 4 and a reaction product of an organoaluminium compound and a cyclic amide, as well as to a process for preparing linear alpha-olefins utilizing this catalyst composition.

13 Claims, No Drawings

CATALYST COMPOSITION AND PROCESS FOR PREPARING LINEAR ALPHA-OLEFINS

The present invention relates to a catalyst composition for oligomerization of ethylene and a process for preparing linear alpha-olefins by oligomerization of ethylene.

Linear alpha-olefins having 4 to 20 carbon atoms are key feedstocks in the production of surfactants, plastisizers, synthetic lubricants and polyolefins. High purity alpha-olefins are particularly valuable in the production of low-density polyethylene and in the oxo process. The linear alpha-olefins are more reactive than the branched alpha-olefins; the branching at the α-carbon decreases the reactivity drastically. In this regard, linear alpha-olefins having 6 to 18 carbon atoms are particularly useful and widely used in large quantities.

Although linear olefins are the product of dehydrogenation of linear alkanes, the major portion of such products consists of the internal olefins. Preparation of alpha-olefins is based largely on oligomerization of ethylene.

These linear alpha-olefins are prepared usually by the catalytic oligomerization of ethylene in the presence of a Ziegler-type catalyst. Ethylene oligomerization produces a wide spectrum of LAO products having even-numbered carbon chain lengths. In recent years the drive to develop more advanced polyethylenes using metallocene catalysts has made extra demands on co-monomer alpha olefins. Co-monomers are used in polyethylene to control density and enhance particular physical properties. Butene-1 and hexene-1 are used in the production of high density polyethylene (HDPE) co-polymers. Butene-1, hexene-1 and octene-1 are used in the production of linear low density polyethylene (LLDPE) co-polymers. The key factor in ethylene oligomerization is to get the desired selectivity and product distribution. Catalyst and process conditions play an important role in this area.

U.S. Pat. No. 3,644,563 discloses the use of a homogeneous organometallic nickel-based catalyst with appropriate bidentate ligands. The ethylene oligomerization is run in polar oxygen-containing solvents such as 1,4-butanediol, in which the catalyst is highly soluble but the end product hydrocarbon oligomers are not. The oligomerization is carried out at 120° C. and 14 MPa (140 bar). The olefins obtained according to this process have a high linearity and their molecular weights follow a Shulz-Flory distribution. The process therefore has disadvantages of requiring rather drastic pressure and temperature conditions, and of giving a wide distribution of alpha olefins. Hexene-1 selectivity is around 13 wt %.

U.S. Pat. No. 4,783,573 discloses a catalytic system based on a zirconium/aluminum complex using anhydrous zirconium chloride with aluminum sesquichloride and triethyl aluminum in dry benzene solvent. These components are stirred under an argon atmosphere over a period of time to form the active catalyst complex. Thiophene is added to the catalyst presumably as a moderator. Examples of oligomerization at 120° C. and 3.4 MPa carried out in dry benzene show an ability to manufacture alpha olefins with long chain lengths, with results as follows: C4—14.9 wt %, C6—15.1 wt %, C8—14.0 wt %, C10-C18—40.2 wt %, C20+—14.2 wt % and wax—1.6 wt %. The disadvantage of the process is a low selectivity of light alpha olefin fractions (particularly hexene-1). Another disadvantage is a high reaction temperature. Hence another disadvantage of a process is benzene which used as a solvent is known carcinogen.

WO 03/050126 A1 describes a zirconium based sulfonic complex combined with an alkylating organometallic compound, for example an alkylaluminumhalide which can be advantageously used as components of a catalyst for the oligomerization of ethylene, for the selective production of primary linear olefins having 4, 6 and 8 carbon atoms respectively. Said oligomerization catalysts particularly oriented towards mixtures of hexene-1 and octene-1 with selectivities in best example is 39 wt % and 25.9 wt %, respectively. The disadvantage of the catalyst is significantly low activity. According to some examples, high Al/Zr ratio (more than 100) is required in order to have a satisfactory catalyst activity.

Further, WO 80/00224 and DE 4338414 also teach a catalyst, which includes a zirconium carboxylate of the general formula $(RCOO)_m ZrCl_{4-m}$ and an organoaluminum compound of the formula $R_n AlX_{3-n}$. The main disadvantages of that catalytic system is the formation of undesired and problematic byproducts such as wax and/or polymer (polyethylene, branched and/or cross-linked PE). The formation of wax and/or polymers, even in small amounts, has a bad impact to the entire technological process on producing oligomers, since by-products not only lower the yield of $C_4$-$C_{20}$ oligomers and its purity, but also reduce the working time of the process equipment, insofar as solid polymer accumulating in the reactors has to be periodically removed, which can be done only by interrupting the oligomerization process and hence, at the expense of lost time of the equipment. Another disadvantage of this catalyst system is the high cocatalyst/activator consumption. The catalyst/co-catalyst ratio is a key parameter that enables the modification of the alpha olefin distribution in this catalyst system. The high catalyst/co-catalyst ratio can favor the low molecular weight oligomers but at the expense of making branched C10+ fractions. The maximum hexene-1 selectivity which can be achieved by using this catalyst system is ~18 wt %.

U.S. Pat. No. 5,496,783 describes a process for converting ethylene to linear alpha olefins in the presence of a catalyst consisting of a zirconium compound with an organic compound chosen from within class of acetals and ketals and with a chlorine or bromine-containing compound of aluminum hydrocarbyl. Although the catalyst has a good selectivity for the formation of light alpha olefins, mainly C4-C10, the distribution of the product among these compounds is too orientated towards the production of butene-1. According to the examples the highest hexene-1 selectivity is about 31 wt %, where butene-1 is around 43 wt %. Another disadvantage of the process is the formation of polymer traces which eventually accumulate in the reactor and prevent a long production run. Hence another disadvantages of the process is a low activity of the catalyst.

It is therefore an object of the present invention to provide a catalyst composition which overcomes the drawbacks of the prior art, especially a catalyst composition shall be provided which can provide equivalent or even greater catalytic activity and increases the selectivity of the hexene-1 fraction.

Additionally, a process for preparing linear alpha-olefins by oligomerization of ethylene shall be provided.

The first object is achieved by a catalyst composition for the oligomerization of ethylene, comprising: (i) at least one transition metal compound having the general formula $MX_m(OR')_{4-m}$ or $MX_m(OOCR')_{4-m}$, wherein R' is an alkyl, alkenyl, aryl, aralkyl or cycloalkyl group, X is chlorine or bromine and m is from 0 to 4; and (ii) a reaction product of an organoaluminum compound and a cyclic amide.

Preferably, the transition metal compound is a zirconium compound.

More preferably, the zirconium compound is a zirconium carboxylate having the formula $(R^2 COO)_m ZrCl_{4-m}$, wherein $R^2$ is alkyl, alkenyl, aryl, aralkyl or cycloalkyl group, and m is any number within the range from 0 to 4.

In one embodiment, the organoaluminum compound has the general formula $R^1{}_n AlX_{3-n}$ or $Al_2X_3R^1{}_3$, wherein R' represents an alkyl group having from 1 to 20 carbon atoms, X represents Cl, Br or I, n is any number within the range $1 \leq n \leq 2$.

Preferably, the organoaluminum compound is $Al(C_2H_5)_3$, $Al_2Cl_3(C_2H_5)_3$, $AlCl(C_2H_5)_2$ or mixtures thereof, wherein $AlCl(C_2H_5)_2$ is preferred.

Moreover preferred is a catalyst composition wherein the cyclic amide has the general structure

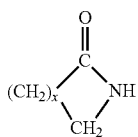

wherein x=1 to 9.

It is further preferred that the cyclic amide is selected from ε-caprolactam, 2-pyrrolidone, δ-valerolactam and mixtures thereof.

Most preferably, the cyclic amide is 2-pyrrolidone having the formula:

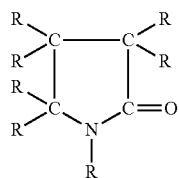

wherein R is independently selected from the group consisting of hydrogen, alkyl having from 1 to 20 carbon atoms, aryl having from 6 to 18 carbon atoms aralkyl having from 7 to 14 carbon atoms and heterocyclyl having from 2 to 9 carbon atoms. More preferably is R hydrogen.

The catalyst composition may additionally comprise an electron donor compound, wherein the electron donor compound is preferably selected from the group consisting of ethyl acetate, ethyl acetoacetate, ethyl benzoate, anisole, tetrahydrofuran, 1,2-dioxane, thiophen and mixtures thereof, wherein anisole is most preferred.

In one embodiment, the molar ratio of the organometallic transition metal compound and the electron donor compound is from 1:0.1 to 1:10, more preferably from 1:0.1 to 1:2.

In another embodiment, the molar ratio of the organoaluminum compound and the cyclic amide is 1:(0.1-1), more preferably 1:(0.1-0.5).

According to the invention is also a process for preparing linear alpha-olefins by oligomerization of ethylene in the presence of an organic solvent and a catalyst composition, wherein the catalyst composition is as disclosed above.

Surprisingly, it was found that the addition of the cyclic amide, i.e. the reaction product with the organoaluminum compound, can alter the product distribution of ethylene oligomerization catalyst systems based on organometallic transition metal compounds and an organoaluminum co-catalyst. The new catalyst composition efforts higher yield of $C_4$-$C_{10}$ portion, particularly $C_6$ fraction with higher purity of alpha-olefins. And at the same time wax/polymer formation in the reactor is significantly reduced. Thus, the present invention describes a catalyst composition for the selective preparation of light alpha-olefins, $C_4$-$C_{10}$, particularly hexene-1, with a high yield. With the process according to the present invention linear alpha-olefins of high linearity of above 90% within a desirable molecular weight range, e.g. oligomers of $C_4$-$C_{10}$, can be produced.

Additionally, it was found that the catalyst composition exhibits high activity and productivity and requires relatively smaller amounts of co-catalyst than prior art catalysts in order to produce linear oligomers in a given molecular weight range. Besides no wax/polymer formation was formed during the process which efforts a long production run.

The catalyst composition used in the production of linear alpha-olefins is preferably utilized in an inert organic solvent. The examples of suitable organic solvents include aromatic hydrocarbon solvents, unsubstituted or substituted with halogens, such as toluene, benzene, xylene, chlorobenzene, dichlorobenzene, chlorotoluene and the like, aliphatic paraffin hydrocarbons, such as pentane, hexane, heptane, octane, nonane, decane and the like, alicyclic hydrocarbon compounds, such as cyclohexane, decahydronaphthalene and the like, halogenated alkanes, such as dichloroethane, dichlorobutane and the like. A mixture of solvents may be used to control the products molecular weight distribution to obtain maximum selectivity to the desired olefin products.

In order to simplify the process of ethylene oligomerization, the organometallic transition metal compound and the optional electron donor can be mixed and kept for at least one year without any changes. Of course, the organometallic transition metal compound can be used without any electron donor for the selective oligomerization of ethylene to $C_4$-$C_{10}$-alpha-olefins. However, it was surprisingly found that the addition of the electron donor to the catalyst composition can further increase the catalyst activity at least by 10% without effecting hexene-1 selectivity.

The co-catalyst, being the reaction product of the organoaluminum compound and the cyclic amide, was very surprisingly found to be useful for selective ethylene oligomerization towards $C_4$-$C_{10}$ fraction with high selectivity of hexene-1.

Additional features and advantages of the present invention will become apparent from the following detailed description of preferred embodiments with regard to the examples.

Experimental Conditions:

All materials were handled in a nitrogen atmosphere using either schlenk techniques or nitrogen filled glove box. Nitrogen and toluene were supplied from a plant source and were dried by an additional bed of molecular sieves, if necessary.

EXAMPLES

The synthesis of zirconium carboxylates are performed by known methods. A component A (zirconium carboxylate) and component B (anisole) were mixed with molar ratio of from about 1:0.1 to about 1:10, more preferably from about 1:0.1 to about 1:2.

A component C (diethyl aluminum chloride, DEAC) and a toluene solution of component D (2-pyrrolidone) were mixed with molar ratio of about C:D=1: (0.1-1), more preferably C:D=1: (0.1-0.5). The toluene solution of 2-pyrrolidone was added slowly dropwise (exothermic reaction) to the diethyl aluminum chloride under a reduced pressure and in the presence of an inert atmosphere (nitrogen).

Oligomerization of Ethylene was Performed as Follows:

The prepared catalyst solution (component A and B, reaction product of C and D) is charged into a 2 liter stainless steel reactor. Ethylene was introduced into the reactor until the desired pressure was attained and maintained throughout the reaction at the desired temperature. Introduction of ethylene was continued in an amount necessary to maintain the reaction pressure. After the reaction was continued for 1 hour with maintaining the reaction conditions, the ethylene feeding is interrupted and the reaction was stopped by the addition of about 20 ml of ethanol. After bringing the temperature of the reaction mixture to 10° C., a sample of the solution was collected, by means of a valve situated at the bottom of the reactor and analyzed by gas chromatography to determine the quantity and the type of olefins formed. After eliminating the overpressure of ethylene, the reactor was opened and examined for any possible polymeric products.

The following examples are given to illustrate the scope of the invention. As will be apparent to those skilled in the art, numerous variations are possible and thus the scope of the invention should not be limited thereto.

The results are summarized in Table 1 & 2.

Example 1

200 ml toluene was placed in a 250 ml round bottom flask and 0.24 mmol Zr (i-$C_3H_7COO$)$_4$ premixed with anisole having molar ratio to 1:0.75 was added to the flask. Then a new co-catalyst solution having molar ratio of components C/D=1:0.15 was added to the mixture. The molar ratio of Al/Zr was 20. The catalyst solution thus formed was then transferred under a stream of inert gas to the reactor. A reaction was conducted at 70° C. and 30 bar ethylene pressure. The oligomerization time was 60 minutes. 269 g of LAO are formed; a yield of 12294 g LAO/g Zr. No wax or polymer was formed.

Example 2

200 ml toluene was placed in a 250 ml round bottom flask and 0.24 mmol Zr (i-$C_3H_7COO$)$_4$ premixed with anisole having molar ratio to 1:0.75 was added to the flask. Then a new cocatalyst solution was added to the mixture with molar ratio components C:D=1:0.25. The molar ratio of Al/Zr was 20. The catalyst solution thus formed was then transferred under a stream of inert gas to a reactor. A reaction was conducted at 70° C. and 30 bar ethylene pressure. The oligomerization time was 60 minutes. 122 g of LAO was formed; a yield of 5575 g LAO/g Zr. No wax or polymer was formed.

Example 3

200 ml toluene was placed in a 250 ml round bottom flask and 0.24 mmol Zr (i-$C_3H_7COO$)$_4$ premixed with anisole having molar ratio to 1:0.75 was added to the flask. Then a new cocatalyst solution was added to the mixture with molar ratio components C:D=1:0.25. The molar ratio of Al/Zr was 20. The catalyst solution thus formed was then transferred under a stream of inert gas to a reactor. A reaction was conducted at 90° C. and 37 bar ethylene pressure. The oligomerization time was 60 minutes. 155 g of LAO was formed; a yield of 7084 g LAO/g Zr. No wax or polymer was formed.

Example 4

200 ml toluene was placed in a 250 ml round bottom flask and 0.24 mmol Zr (i-$C_3H_7COO$)$_4$ premixed with anisole having molar ratio to 1:0.75 was added to the flask. Then a new cocatalyst solution was added to the mixture with molar ratio components C:D=1:0.17. The molar ratio of Al/Zr was 40. The catalyst solution thus formed was then transferred under a stream of inert gas to a reactor. A reaction was conducted at 60° C. and 30 bar ethylene pressure. The oligomerization time was 60 minutes. 129 g of LAO was formed; a yield of 5895 g LAO/g Zr. No wax or polymer was formed.

Example 5

200 ml toluene was placed in a 250 ml round bottom flask and 0.24 mmol Zr (i-$C_3H_7COO$)$_4$ was added to the flask. No anisole was used this time. Then a new co-catalyst solution was added to the mixture with molar ratio of components C:D=1:0.15. The molar ratio of Al/Zr was 20. The catalyst solution thus formed was then transferred under a stream of inert gas to a reactor. A reaction was conducted at 70° C. and 30 bar ethylene pressure. The oligomerization time was 60 minutes. 210 g of LAO was formed; a yield of 9597 g LAO/g Zr. No wax or polymer was formed.

Example 6

Comparative 200 ml toluene, 0.25 mmol of Zr(i-$C_3H_7COO$)$_4$ and neat diethyl aluminum chloride (DEAC) (Al/Zr=40) were mixed in a 250 ml round bottom flask. The catalyst solution thus formed was then transferred under a stream of inert gas to a reactor. Reaction was conducted at 60° C. and 30 bar ethylene pressure. Oligomerization time is 60 minutes. 370 g of LAO and 0.3 g of byproduct polyethylene was formed; a yield of 16228 g LAO/g Zr. A high amount of wax was formed which could not be correctly analysed by GC.

Example 7

Comparative 200 ml toluene, 0.25 mmol of Zr(i-$C_3H_7COO$)$_4$ and neat ethyl aluminum sesquichloride (EASC) (Al/Zr=35) were mixed in a 250 ml round bottom flask. The catalyst solution thus formed was then transferred under a stream of inert gas to the reactor. The reaction was conducted at 80° C. and 30 bar ethylene pressure. Oligomerization time was 60 minutes. 213 g of LAO was formed; a yield of LAO 9342 g/g Zr. Traces of solid polymer were observed.

Example 8

Comparative

The same procedure as in Example 7 was repeated, except that Al/Zr=17.5. Reaction was conducted at 80° C. and 30 bar ethylene pressure. Oligomerization time was 60 minutes. 460 g of LAO and 0.2 g of byproduct polyethylene are formed; a yield of 20175 g LAO/g Zr. A high amount of wax was formed which could not be correctly analysed by GC.

TABLE 1

Summary of the Oligomerization Experiments

| Examples | Distribution of alpha olefins (wt %) | | | | | |
| --- | --- | --- | --- | --- | --- | --- |
|  | C4 | C6 | C8 | C10 | C12-C18 | C20+ |
| Example1 | 34.1 | 40.3 | 13.5 | 6 | 6 | 0.1 |
| Example2 | 36 | 48.2 | 10.3 | 3 | 2.4 | 0.1 |
| Example3 | 25.9 | 48.6 | 14.6 | 5.5 | 5 | 0.4 |
| Example4 | 22.6 | 57.8 | 13.3 | 3.7 | 2.4 | 0.2 |
| Example5 | 22 | 41.8 | 16.6 | 8.1 | 10.2 | 1.3 |
| Example6(comparative) | 28.5 | 12.3 | 13.5 | 13.4 | 20.2 | 12.1 |
| Example7 (comparative) | 34.9 | 18.5 | 15.8 | 11.6 | 17.1 | 2.1 |

TABLE 1-continued

Summary of the Oligomerization Experiments

| | Distribution of alpha olefins (wt %) | | | | | |
|---|---|---|---|---|---|---|
| Examples | C4 | C6 | C8 | C10 | C12-C18 | C20+ |
| Example8 (comparative) | 13.8 | 10.4 | 10.8 | 12.1 | 39 | 13.9 |

TABLE 2

Summary of the Oligomerization Experiments

| | Purity of LAO fractions (%) | | | | |
|---|---|---|---|---|---|
| Examples | C4 | C6 | C8 | C10 | C12 |
| Example 1 | 99.5 | 98.1 | 98.7 | 91.7 | 90.8 |
| Example 2 | 99.4 | 98.9 | 97.5 | 92.3 | 91.2 |
| Example 3 | 99.9 | 98.5 | 98.5 | 91.1 | 90.5 |
| Example 4 | 98.2 | 97.8 | 98 | 91 | 90.8 |
| Example 5 | 99.1 | 97.3 | 98.5 | 91 | 90.5 |
| Example 6 (comparative) | 97.3 | 93.2 | 92.5 | 86.3 | 85.8 |
| Example 7 (comparative) | 98.2 | 96.1 | 95 | 88.2 | 86 |
| Example 8 (comparative) | 98.1 | 97.1 | 94.8 | 91.1 | 90.5 |

As can be taken from Tables 1 and 2, the oligomerization experiments according to the examples of the present invention result in an improved distribution of alpha-olefins (weight percent) with a high amount of $C_6$. Additionally, the purity of the LAO fractions is significantly improved compared to the results of the comparative examples.

The features disclosed in the foregoing description and in the claims may, both separately and in any combination thereof, be material for realizing the invention in diverse forms thereof.

The invention claimed is:

1. A catalyst composition for the oligomerization of ethylene, consisting essentially of:
    (i) at least one transition metal compound having the general formula $MX_m(OR')_{4-m}$ or $MX_m(OOCR')_{4-m}$, wherein M is a transition metal, R' is an alkyl, alkenyl, aryl, aralkyl or cycloalkyl group, X is chlorine or bromine and m is an integer from 0 to 4; and
    (ii) a reaction product of an organoaluminum compound and a cyclic amide having the general structure:

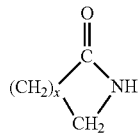

wherein x=1 to 9, wherein the transition metal compound is a zirconium compound.

2. The catalyst composition according to claim 1, wherein the zirconium compound is a zirconium carboxylate having the formula $(R^2COO)_m ZrCl_{4-m}$, wherein $R^2$ is an alkyl, alkenyl, aryl, aralkyl or cycloalkyl group, and m is an integer within the range 1 to 4.

3. The catalyst composition according to claim 2, wherein the organoaluminum compound has the general formula $R^1_n AlX_{3-n}$ or $Al_2 X_3 R^1_3$, wherein $R^1$ represents an alkyl group having from 1 to 20 carbon atoms, X represents Cl, Br or I, n is 1 or 2.

4. The catalyst composition according to claim 2, wherein the organoaluminum compound comprises $Al(C_2H_5)_3$, $Al_2Cl_3(C_2H_5)_3$, $AlCl(C_2H_5)_2$, and mixtures thereof.

5. The catalyst composition according to claim 4, wherein the organoaluminum compound comprises $AlCl(C_2H_5)_2$.

6. The catalyst composition according to claim 4, wherein the cyclic amide is selected from the group consisting of ε-caprolactam, 2-pyrrolidone, δ-valerolactam and mixtures thereof.

7. The catalyst composition according to claim 4, additionally comprising an electron donor compound selected from the group consisting of ethyl acetate, ethyl acetoacetate, ethyl benzoate, anisole, tetrahydrofuran, 1,2-dioxane, thiophen and mixtures thereof.

8. The catalyst composition according to claim 7, wherein the electron donor compound comprises anisole.

9. The catalyst composition according to claim 7, wherein the molar ratio of the transition metal compound and the electron donor compound is from 1:(0.1-2).

10. The catalyst-composition according to claim 9, wherein the molar ratio of the organoaluminum compound and the cyclic amide is from 1:(0.1-0.5).

11. The catalyst composition according to claim 6, further comprising an electron donor compound selected from the group consisting of ethyl acetate, ethyl acetoacetate, ethyl benzoate, anisole, tetrahydrofuran, 1,2-dioxane, thiophen and mixtures thereof.

12. The catalyst composition according to claim 11, wherein the molar ratio of the transition metal compound and the electron donor compound is from 1:(0.1-2.0) and the molar ratio of the organoaluminum compound and the cyclic amide is from 1:(0.1-0.5).

13. A process for the oligomerization of ethylene, comprising contacting ethylene with the catalyst composition of claim 1 under ethylene oligomerization conditions.

* * * * *